US012152281B2

(12) United States Patent
Peltonen et al.

(10) Patent No.: US 12,152,281 B2
(45) Date of Patent: Nov. 26, 2024

(54) GENE THERAPY VECTOR CONTAMINATION ASSAY

(71) Applicant: Trizell Ltd., Chinnor (GB)

(72) Inventors: Hanna Peltonen, Kuopio (FI); Jenni Mykkanen, Kuopio (FI); Minna Hassinen, Kuopio (FI); Seppo Yla-Herttuala, Kuopio (FI); Nigel Parker, Chinnor (GB)

(73) Assignee: Trizell Ltd., Chinnor (GB)

( * ) Notice: Subject to any disclaimer, the term of this patent is extended or adjusted under 35 U.S.C. 154(b) by 0 days.

(21) Appl. No.: 16/426,124

(22) Filed: May 30, 2019

(65) Prior Publication Data
US 2019/0292609 A1 Sep. 26, 2019

(51) Int. Cl.
*C12Q 1/686* (2018.01)
*C12Q 1/6888* (2018.01)
*C12Q 1/70* (2006.01)

(52) U.S. Cl.
CPC .......... *C12Q 1/6888* (2013.01); *C12Q 1/686* (2013.01); *C12Q 1/701* (2013.01); *C12Q 2531/113* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 6,020,191 | A | 2/2000 | Scaria et al. | |
|---|---|---|---|---|
| 6,805,858 | B1 * | 10/2004 | Zhang | A61K 38/1709 424/93.1 |
| 2008/0193484 | A1 | 8/2008 | Wang et al. | |
| 2016/0215354 | A1 | 7/2016 | Dorange | |
| 2019/0002842 | A1 | 1/2019 | Lock et al. | |

FOREIGN PATENT DOCUMENTS

| EP | 2553105 A0 | 2/2013 |
|---|---|---|
| WO | WO-2001/044280 A2 | 6/2001 |
| WO | 2003104476 A2 | 12/2003 |
| WO | WO-2008/079354 A2 | 7/2008 |
| WO | WO/13/163545 * | 10/2013 |
| WO | WO-2020/242913 A1 | 12/2020 |

OTHER PUBLICATIONS

Boehme et al., Standard Free Droplet Digital Polymerase Chain Reaction as a New Tool for the Quality Control of High-Capacity Adenoviral Vectors in Small-Scale Preparations, 2015, Human Gene Therapy Methods, vol. 26, pp. 25-34.*
International Search Report for PCT/US2020/034146, 5 pages (dated Oct. 16, 2020).
Written Opinion for PCT/US2020/034146, 6 pages (dated Oct. 16, 2020).
Dong Guiwei et al.: "Development and evaluation of a droplet digital PCR assay for the detection of fowl adenovirus serotypes 4 and 10 in attenuated vaccines", Journal of Virological Methods, Elsevier BV, NL, vol. 265, Sep. 14, 2018 (Sep. 14, 2018), pp. 59-65, XP085584504.
Li Qiuchen et al.: "A New Strategy for the Detection of Chicken Infectious Anemia Virus Contamination in Attenuated Live Vaccine by Droplet Digital Pcr", Biomed Research International, vol. 2019, May 16, 2019 (May 16, 2019), pp. 1-9, XP093051972, ISSN: 2314-6133, DOI: 10.1155/2019/2750472 Retrieved from the Internet: URL:https://downloads.hindawi.com/journals /bmri/2019/2750472.pdf>.
Hehir K M et al.: "Molecular Characterization of Replication-Competent Variants of Adenovirus Vectors and Genome Modifications To Prevent Their Occurrence", Journal of Virology, the American Society for Microbiology, US, vol. 70, No. 12, Dec. 1, 1996 (Dec. 1, 1996), pp. 8459-8467, XP002911790.
Wrzesinski Claudia et al.: "Chimeric and Pseudotyped Parvoviruses Minimize the Contamination of Recombinant Stocks with Replication-Competent Viruses and Identify a DNA Sequence That Restricts Parvovirus H-1 in Mouse Cells", Journal of Virology, vol. 77, No. 6, Mar. 15, 2003 (Mar. 15, 2003), pp. 3851-3858, XP093090315.
Polo John M et al.: "Stable alphavirus packaging cell lines for Sindbis virusand Semliki Forest virus-derived vectors", Apr. 13, 1999 (Apr. 13, 1999), XP093090322, Retrieved from the Internet: URL:https://www.pnas.org/doi/abs/10.1073/p nas.96.8.4598.
Kenneth Cornetta et al.: "Absence of Replication-Competent Lentivirus in the Clinic: Analysis of Infused T Cell Products", Molecular Therapy, vol. 26, No. 1, Sep. 12, 2017 (Sep. 12, 2017), pp. 280-288, XP055574573.
European Patent Office, Supplementary Search Report for EP Application No. EP20812945, completed Oct. 11, 2023.
European Patent Office, Supplementary Partial Search Report for EP Application No. EP20812945, completed Jun. 7, 2023.
European Patent Office, European Search Opinion for EP Application No. EP20812945, completed Oct. 19, 2023.

* cited by examiner

*Primary Examiner* — Benjamin P Blumel
(74) *Attorney, Agent, or Firm* — Casimir Jones SC; Lisa Mueller

(57) ABSTRACT

Certain viral gene therapy vectors are by design unable to replicate in a patient. Nonetheless, during manufacture of viral gene therapy vector, undesirable replication-competent virus ("RCV") may form due to random mutation or other events. Viral gene therapy vector manufacturers thus assay for the presence of contaminating RCV. Regulatory agencies require this to be done by assaying for serial infection, i.e., transducing target cells with the viral vector, and then lysing the transduced cells, and then mixing the lysate with live assay cells, and then microscopically observing the assay cells to visually determine whether they have been infected with virus. We have tested various alternative approaches, and surprisingly found that digital PCR is not only faster than the prior art approach, but is also over an order of magnitude more sensitive, able to detect, for example, in $3 \times 10^{10}$ assay cells, as few as seven (7) replication competent adenoviruses ("RCA").

10 Claims, 2 Drawing Sheets
Specification includes a Sequence Listing.

SEQUENCE LISTING

```
<160> NUMBER OF SEQ ID NOS: 3

<210> SEQ ID NO 1
<211> LENGTH: 21
<212> TYPE: DNA
<213> ORGANISM: Adenovirus type 5

<400> SEQUENCE: 1
aaccagttgc cgtgagagtt g                                          21

<210> SEQ ID NO 2
<211> LENGTH: 24
<212> TYPE: DNA
<213> ORGANISM: Adenovirus type 5

<400> SEQUENCE: 2
ctcgttaagc aagtcctcga taca                                       24

<210> SEQ ID NO 3
<211> LENGTH: 19
<212> TYPE: DNA
<213> ORGANISM: Adenovirus type 5

<400> SEQUENCE: 3
tgggcgtcgc caggctgtg                                             19
```

GENE THERAPY VECTOR CONTAMINATION ASSAY

CROSS-REFERENCE TO RELATED APPLICATIONS

Not applicable

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

REFERENCE TO A SEQUENCE LISTING

This application incorporates by reference the Patent In™ file of record in this application.

STATEMENT REGARDING PRIOR DISCLOSURES BY THE INVENTOR OR A JOINT INVENTOR

Not applicable

BACKGROUND

Certain viral gene therapy vectors are by design unable to replicate in a patient. For example, to replicate in normal human cells, an adenovirus requires functioning E1a, E1b and E3 genome regions. Viral gene therapy vectors may be made replication deficient by deleting or mutating these regions.

Nonetheless, during manufacture of viral gene therapy vector, undesirable replication-competent virus ("RCV") may form due to random mutation or other events. For example, E1a-deleted adenoviral vector may be manufactured in HEK293 cells, which contain a functional E1a region. Spontaneous recombination may theoretically add a functional E1a region back into an adenovirus, create a replication competent adenovirus ("RCA").

Viral gene therapy vector manufacturers thus assay replication-deficient viral vector for the presence of contaminating RCV. Regulatory agencies, i.e., the European Medicines Agency and The United States Food & Drug Administration, require this to be done by assaying for serial infection using what is commonly called a "roller bottle" assay.

In this method, target cells (e.g., HEK cells) are grown in culture medium. A sample of the viral vector is then added to transduce the target cells, and the cells are cultured long enough to allow transduction to complete. The target cells are then pelleted and rinsed to remove any residual viral vector in the media. The target cells are then lysed, and the lysate is added to a culture of assay cells (e.g., HeLa cells). The assay cells are then grown in media for a long enough time to enable infectious virus (if any) to produce visible infection of the assay cells. Optionally, these assay cells may be again pelleted, rinsed, lysed and the lysate added to a second culture of assay cells, which are in turn grown in media. Visible infection is determined microscopically, observing the assay cells to visually determine whether they have been infected with virus. That visual inspection is an assessment of visible cellular stress; infect cells become visibly deformed and look poorly, while in the absence of infectious virus the assay cells look normal. This test is often referred to as a "roller bottle" test because the assay cells are typically cultured in roller bottles.

The roller bottle assay has been understood to be sensitive enough to detect <1 RCA in $3 \times 10^{10}$ viral particles. The roller bottle test is somewhat subjective because it relies on microscopic observation of assay cells' morphology. To find a more objective assay, we tested various alternative approaches. In comparing alternative assays to the industry-standard roller bottle assay, we surprisingly found that, contrary to the teachings of the art, the roller bottle assay is not sensitive enough to detect <1 RCA in $3 \times 10^{10}$ viral particles. To the contrary, we have found that the roller bottle assay is only able to detect $\geq 75$ RCA in $3 \times 10^{10}$ viral particles.

We thus have invested the time to develop an alternative approach using digital PCR. This can be faster than the prior art approach, provides more objective data and, surprisingly, is an order of magnitude more sensitive, able to detect, for example, as few as seven (7) RCA in $3 \times 10^{10}$ viral particles.

BRIEF SUMMARY

This disclosure describes an assay to detect replication competent virus ("RCV"), for example replication competent adenovirus ("RCA"), with digital polymerase chain reaction (dPCR). Preferably, one may use droplet digital PCR (ddPCR) because the equipment is readily available. Our assay contains multiple amplification cycles of RCA in cell culture and detection of the amplified RCA by ddPCR method.

The patent or application file contains at least one drawing executed in color. Copies of this patent or patent application publication with color drawing(s) will be provided by the Office upon request and payment of the necessary fee.

DETAILED DESCRIPTION

Figure 1:
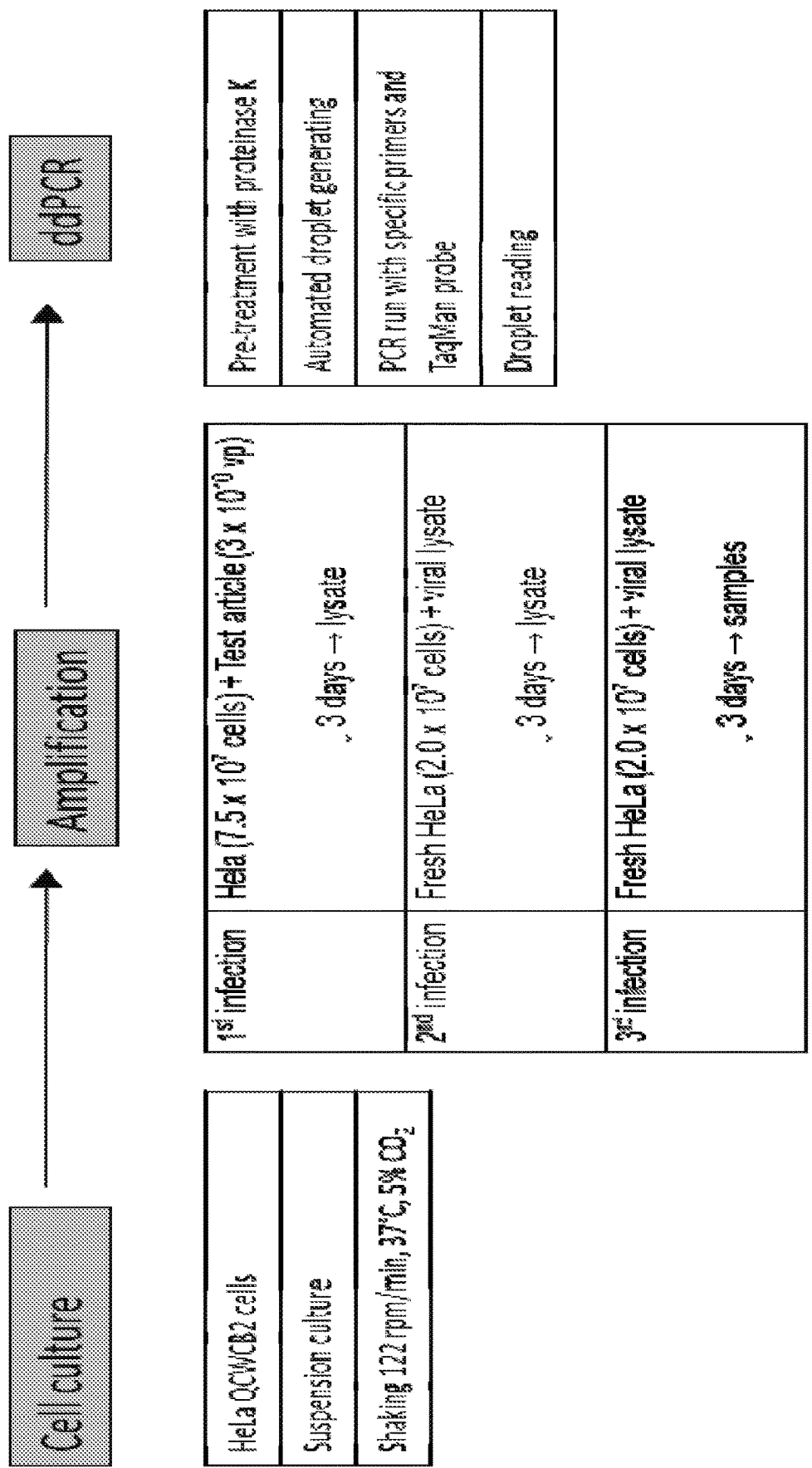
FIG. 1 provides a flow chart overview of our assay.

Our assay is outlined in FIG. 1. In FIG. 1, suspension-cultured HeLa cells are used to amplify possible RCA. The cells are seeded into 500 ml shaker flasks at a density of $7.5 \times 10^{7}$ cells/flask. To each flasks is added $3 \times 10^{10}$ virus particles (vp) of test sample (TS). After three days of incubation (+37° C., 5% $CO_2$, 122 rpm), the cells are collected and lysed with three freeze-thaw cycles. The lysate is cleared by centrifugation.

The lysate is then added to 125 ml shaker flasks of fresh assay cells ($2 \times 10^{7}$ cells/flask). These first assay culture flasks are handled the same way as the target cell culture.

The lysate from the first assay culture is then added to a second assay culture ($2 \times 10^{7}$ cells/flask. After three days of incubation, the second assay culture cells are collected and lysed. The lysate is cleared by centrifugation and stored in ultra-low temperature freezer. Multiple RCA amplification cycles are performed to minimize interfering effects of therapeutic protein (e.g., transgene in the viral vector coding for, for example, interferon, which would impede growth of interferon-sensitive assay cells) and to maximize RCA yield.

RCA in the lysate is detected by digital polymerase chain reaction (dPCR) method. We prefer to use ddPCR, and thus discuss it below, but other dPCR methods may be used as well.

The lysate is pre-treated with proteinase K to release viral DNA encapsulated inside the viral particles.

The pre-treated lysate is used as a sample in ddPCR analysis with PCR primers and a probe (e.g., a TaqMan probe) specific for a part of the viral genome region which has been delted from the virus (to render it replication-incompetent) For example, we have used this method to assay an adenovirus from which the E1 region has been deleted. The E1 region is essential for the adenovirus replication and is therefore deleted from the genome of various adenoviral gene therapy vectors, but is present in the wild-type (infective) genome.

In our ddPCR analysis, we prepared a mixture including supermix, primers and probe, and then pipetted it on triplicate wells on a 96-well plate. The lysate sample (from above) is added on each of the wells. We then used an automated droplet generator to generate thousands of small droplets. The sample DNA randomly divides between the droplets. The DNA inside the droplets is amplified by PCR. The droplets are read using a reader which counts positive and negative droplets. The result is calculated using Poisson distribution and given as copies/µl.

We have used this protocol for replication-deficient adenovirus gene therapy vector, but conceptually one may use it for any other replication-deficient virus which has a genome amenable to PCR analysis. Similarly, we have tested this system on viral vector containing a transgene for vascular endothelial growth factor D ("VEGF-D"), but one may use it with vector having another transgene.

As reference standard (RS) for the assay, we used Phase I clinical-grade material at a density of $1.77 \times 10^{11}$ vp/ml. RS is treated similarly to test sample (TS). We prepared duplicate RS flasks. The results of TS are reported against the reference standard.

Amplification is controlled by a negative control (NC). NC is prepared by "mock-infecting" the cells with cell culture medium. NC is prepared as a single flask because we know the expected result.

We used a positive control (PC) prepared by infecting the target cells with 100 vp of wild-type (replication-competent) adenovirus reference material ("ARM"), ATCC catalog No. VR-1516. We use PC for trending purposes only, preparing PC in duplicate.

ddPCR is controlled by a no-template control (NTC). In the NTC, the sample is replaced by the same cell culture medium which was used to dilute the samples, and a positive control of purified ARM DNA (in which cell-free DNA which was extracted from ARM material is used as the sample). We used an original concentration of ARM DNA of 322.1 ng/µl. The ARM DNA was then diluted to 10 ng/µl and aliquoted to aliquots of 12 µl/tube. The aliquots were stored at −20° C. Each aliquot should be thawed no more than five (5) times to minimize freeze-thaw damage to the DNA. We prefer to memorialize or record each thawing on the thawed tube, and discard and aliquot after the 5$^{th}$ thawing.

The assay uses HeLa QCWCB2 cells cultured in DMEM supplemented with 10% FBS /Pen/Strep/L-glutamine. The cells are cultured in suspension shaker flasks of different sizes in e.g., a $CO_2$ incubator equipped with a shaker platform or a New Brunswick S41i™ incubator shaker.

We have found the process is most efficient if performed by two operators on the days of first infection, second infection and third infection. One operator seeds HeLa suspension cells for the assay (7 to 15 flasks for infection and 1 to 5 flasks for further culturing). Another operator prepares viral dilutions for first infection or lyses infected cells during second and third infection. Only one operator is required for harvest and for dPCR analysis.

Cell Culture

Cell culturing is performed according to aseptic technique. HeLa QCWCB2 cells were cultured in suspension. The number of cell flasks required for RCA assay depends on the number of TS to be analyzed. One flask is reserved for NC, two flasks for RS and two flasks for PC. Each TS will be analyzed as duplicates. Maximum of five TSs can be analyzed in one assay (in total 15 flasks).

In order to have the required number of flasks, the culture needs to be adequately scaled up. Table I presents our recommended minimal number of flasks to be seeded to start the assay with different number of test samples (TSs). Shaker flasks of 250 ml and 500 ml are interchangeable so that one 500 ml flask corresponds to two 250 ml flasks. Note that the scaling up needs to be started early enough to obtain required amount of cells: for assays with 4-5 TS, this means roughly two weeks before starting the assay, and for assays with 1-3 TS the preceding week.

TABLE I

Scaling up HeLa suspension culture for RCA assay

| | | | Number of flasks | | | | | |
|---|---|---|---|---|---|---|---|---|
| Week | Day | Task | For 5 TS | For 4 TS | For 3 TS | For 2 TS | For 1 TS | Size of flasks |
| 1 | Thu/Fri | Cell culturing | 2 | 2 | 1 | 1 | 1 | 250 ml |
| 2 | Mon/Tue | Cell culturing | 4 | 4 | 3 | 3 | 2 | 250 ml |
| 2 | Fri | Cell culturing | 9 | 8 | 7 | 5 | 4 | 500 ml |
| 3 | Tue | First infection | 15 | 13 | 11 | 9 | 7 | 500 ml |
| | | | 5 | 4 | 4 | 3 | 3 | 250 ml |
| 3 | Fri | Second infection | 15 | 13 | 11 | 9 | 7 | 125 ml |
| | | | 4 | 4 | 3 | 3 | 2 | 250 ml |
| 4 | Mon | Third infection | 15 | 13 | 11 | 9 | 7 | 125 ml |
| | | | 1 | 1 | 1 | 1 | 1 | 250 ml |

The recommended minimal number of flasks to be seeded to start the assay with different number of test samples (TS) are presented. Scaling up should be started 1-2 weeks before the assay. Week days are exemplary and can be adjusted as needed. The flasks needed for the assay are indicated; additionally, multiple flasks need to be seeded for further culturing at the same time.

Before seeding the cells for RCA assay, the growth of the culture is monitored and the cells are counted. We prefer to use the following system suitability criteria (SSC) for cells: cell viability ≥80%, and RSD % (Relative Standard Deviation) of cell counting, ≤20%.

When seeding the cells to be infected in RCA assay, we prefer to use seeding parameters as presented in Table II.

TABLE II

Cell seeding parameters for RCA assay

| RCA assay step | Size of flask | cells/flask | Volume/flask (ml) |
|---|---|---|---|
| First infection | 500 ml | 1.00E+08 | 100[1] |
| Second infection | 125 ml | 2.00E+07 | 40 |
| Third infection | 125 ml | 2.00E+07 | 40 |

[1] 100 ml of medium will be added 90 ± 10 min after the infection

We prefer the first infection be performed in 500 ml flasks with $1\times10^8$ cells/flask. This cell amount is seeded in 100 ml of medium. After the infection, 100 ml of medium is added. The final cell density in the flask is $5\times10^5$ cells/ml. Test article dose per one flask is $3\times10^{10}$ vp. The dose per cell is 300 vp/cell. The second and the third infection are performed in 125 ml flasks with $2\times10^7$ cells/flask in 40 ml of medium. The cell density is $5\times10^5$ cells/ml. The seeded cells are infected on the same day.

First Infection/Transduction:

For the first infection (or "transduction" where a recombinant virus with a transgene is used), viral vector dilutions are prepared in cold medium (taken from refrigerator). Throughout the protocol cross-contamination is avoided. The virus samples are handled in the following order as applicable: 1) NC, 2) TSs, 3) RS, 4) PC.

a) Mark virus titers (vp/ml).
b) Calculate virus dilutions.
c) Synchronize the work with the operator seeding the cells so that the virus dilutions and the cells to be infected are ready approximately at the same time.
d) Thaw RS, ARM and TSs in refrigerator and keep them cold until immediately before use.
e) Take the needed volume of cold medium into 50 ml tube. The needed volume is as follows: approximately 7.0 ml for preliminary dilutions of PC, approximately 8.5 ml for final dilutions for NC, RS and PC flasks, and approximately 4.5 ml for each TS. (As a result approximately 20 ml is needed for one TS and approximately 40 ml for five TS).
f) Prepare preliminary dilutions of PC (ARM) according to Table III. We have found that ARM has to be heavily diluted by a dilution series in order to achieve desired doses in appropriate volumes. Each dilution needs to be thoroughly mixed before using it to prepare the next one.

TABLE III

Dilution series of ARM

| Dilution | Dilution Factor | Dilution to be used | Volume of dilution (µl) | Volume of medium (µl) | Total volume (µl) | Final conc. (vp/ml) |
|---|---|---|---|---|---|---|
| Dil1 | 100 | Neat | 10 | 990 | 1 000 | $5.8 \times 10^9$ |
| Dil2 | 100 | Dil1 | 10 | 990 | 1 000 | $5.8 \times 10^7$ |
| Dil3 | 100 | Dil2 | 10 | 990 | 1 000 | $5.8 \times 10^5$ |
| Dil4 | 100 | Dil3 | 10 | 990 | 1 000 | $5.8 \times 10^3$ |
| PC | 58 | Dil4 | 43 | 2457 | 2 500 | 100 |

Neat ARM ($5.8 \times 10^{11}$ vp/ml) will be used to prepare Dilution 1. The following Dilutions 2-4 and the final PC will be prepared by using the preceding ones.

g) Prepare final dilutions. Pipet medium first to all the tubes, then test articles, RS and PC only as the last one. Note that two replicate dilution are prepared for RS, PC and each TS. Use the dilutions within 90 minutes from preparation.
h) Infect 500 ml shaker flasks with $1\times10^8$ cells in 100 ml of medium with medium (NC) and with final dilutions. Use all of the dilution (2 ml) for infection.
i) Approximately 90 minutes (±10 min) after the infection, add 100 ml of fresh pre-warmed medium into the flasks with infected cells.
j) Incubate the flasks with the infected cells for three days (+37° C., 5% $CO_2$, 122 rpm).

Note that the assay can be paused after the first infection. Follow the steps a)-h) above. Transfer the supernatants into clean 15 ml sterile centrifuge tubes. Freeze the tubes quickly with liquid nitrogen and store in ultra-low freezer for maximum of two months. On the day of second infection, thaw the frozen supernatants in refrigerator and use all of the supernatants for infecting fresh cells.

Second Infection:

For the second infection, medium (taken from refrigerator) is needed for re-suspending the cells. The virus samples are handled in the following order as applicable: 1) NC, 2) TSs, 3) RS, 4) PC.

a) Synchronize the work with the operator seeding the cells so that the supernatant for infection and the cells to be infected are ready approximately at the same time.
b) Fill liquid nitrogen container up with liquid nitrogen.
c) Transfer infected cell suspension (200 ml) from each of the shaker flasks into 50 ml sterile tubes (4 tubes/sample).
d) Centrifuge the cells down 1 000×g for 10 min at +4° C.
e) Remove supernatants.
f) Re-suspend cell pellets of one sample with 5 ml of fresh cold medium. Add the medium in one tube, re-suspend the pellet by pipetting, transfer the suspension to the second tube of the same sample, re-suspend again and repeat until all four tubes of the sample are handled.
g) Transfer the suspension into 15 ml sterile centrifuge tubes (1 tube/sample).
h) Lyse the cells by 3 cycles of freezing with liquid nitrogen (approximately 5 min) and thawing in water bath at +37° C. (approximately 10 min). The tubes are placed in a metallic cage which can be immersed in liquid nitrogen and in warm water in a row. After each freezing, check that the tubes are intact before placing them in warm water. After each thawing, confirm again that there is no cracks in the tubes and vortex the tubes at low speed. The work can be paused during one of the freezing steps. Keep the samples frozen (liquid nitrogen/−80° C.) until you are ready to continue.
i) Centrifuge the lysed cells 2 000×g for 20 min at +4° C. to get rid of the cell debris. Retain the supernatants.
j) If HeLa suspension cells to be infected are not ready, the supernatants are transferred into clean tubes and kept cold (refrigerator) until the cells are ready.
k) Infect 125 ml shaker flasks with $2\times10^7$ cells in 40 ml with the supernatant. Use all of the supernatants (approximately 5 ml) for infection.
l) Incubate the flasks with the infected cells for three days (+37° C., 5% $CO_2$, 122 rpm).

The assay can be paused after the second infection. Follow the steps a)-h) above. Transfer the supernatants into clean 15 ml sterile centrifuge tubes. Freeze the tubes quickly with liquid nitrogen and store in ultra-low freezer for maximum of two months. On the day of third infection, thaw the frozen supernatants in refrigerator and use all of the supernatants for infecting fresh cells.

Third Infection:

For the third infection, cold medium (taken from refrigerator) is used for re-suspending the cells. The virus samples are handled in the following order as applicable: 1) NC, 2) TSs, 3) RS, 4) PC.

a) Synchronize the work with the operator seeding the cells so that the supernatant for infection and the cells to be infected are ready approximately at the same time.
b) Fill liquid nitrogen container up with liquid nitrogen.
c) Transfer infected cell suspension (40 ml) from each of the shaker flasks into 50 ml sterile tubes (1 tube/sample).
d) Centrifuge the cells down 1 000×g for 10 min at +4° C.
e) Remove supernatants.

f) Re-suspend cell pellets of one sample with 2 ml of fresh cold medium. If the pellets are very dense and hard to re-suspend, the re-suspending volume can be increased.

g) Transfer the suspension into 15 ml sterile centrifuge tubes (1 tube/sample).

h) Lyse the cells by 3 cycles of freezing with liquid nitrogen (approximately 5 min) and thawing in water bath at +37° C. (approximately 10 min). The tubes are placed in a metallic cage which can be immersed in liquid nitrogen and in warm water in a row. After each freezing, check that the tubes are intact before placing them in warm water. After each thawing, confirm again that there is no cracks in the tubes and vortex the tubes at low speed. The work can be paused during one of the freezing steps. Keep the samples frozen (liquid nitrogen/−80° C.) until you are ready to continue.

i) Centrifuge the lysed cells 2 000×g for 20 min at +4° C. to get rid of the cell debris. Keep the supernatant.

j) If HeLa suspension cells to be infected are not ready, the supernatants are transferred into clean tubes and kept cold (refrigerator) until the cells are ready.

k) Infect 125 ml shaker flasks with $2 \times 10^7$ cells in 40 ml with the supernatant. Use all of the supernatants (approximately 2 ml) for infection.

l) Incubate the flasks with the infected cells for three days (+37° C., 5% $CO_2$, 122 rpm).

Harvest:

To harvest, sample labels may be printed according to Table IV. Each flask of infected cells needs four labels: two with aliquot size of 110 µl and two with <1000 µl

TABLE IV

Example labels for harvest aliquots

|  | Example 1 | Example 2 |
|---|---|---|
| RCA-yy-nnn | RCA-19-001 | RCA-19-002 |
| DD-MMM-YYYY/Initials | 21-FEB-2019/HP | 17-JAN-2019/MJK |
| Sample name | NC | TS1_1 |
| Aliquot size | 110 µl | <1000 µl |

Cold medium (taken from refrigerator) is needed for re-suspending the cells. The virus samples are handled in the following order as applicable: 1) NC, 2) TSs, 3) RS, 4) PC.

a) Fill liquid nitrogen container up with liquid nitrogen.

b) Label 1 ml cryotubes for harvest aliquots.

c) Transfer infected cell suspension (40 ml) from each of the shaker flasks into 50 ml sterile tubes (1 tube/sample).

d) Centrifuge the cells down 1 000×g for 10 min at +4° C.

e) Remove supernatants.

f) Re-suspend cell pellets of one sample with 2 ml of fresh cold medium. If the pellets are very dense and hard to re-suspend, the re-suspending volume can be increased.

g) Transfer the suspension into 15 ml sterile centrifuge tubes (1 tube/sample).

h) Lyse the cells by 3 cycles of freezing with liquid nitrogen (approximately 5 min) and thawing in water bath at +37° C. (approximately 10 min). The tubes are placed in a metallic cage which can be immersed in liquid nitrogen and in warm water in a row. After each freezing, check that the tubes are intact before placing them in warm water. After each thawing, confirm again that there is no cracks in the tubes and vortex the tubes at low speed. The work may be paused during one of the freezing steps. Keep the samples frozen (liquid nitrogen/−80° C.) until you are ready to continue.

i) Centrifuge the lysed cells 2 000×g for 20 min at +4° C. to get rid of the cell debris. Keep the supernatants.

j) Transfer the supernatants into new clean tubes and mix.

k) Aliquot the supernatant of each sample into pre-labeled 1 ml cryotubes: 2×110 µl; 2×<1000 µl.

l) Freeze the aliquots quickly with liquid nitrogen and store in freezer until analyzed.

Digital PCR Analysis:

DNA work should be performed under nuclease free conditions. Sterile nuclease-free solutions and plastic ware must be used. Gloves must be worn at all times when handling DNA samples. DNA-ExitusPlus™ may be used to remove possible DNA residues after work. After cleaning the laminar flow hood ("LFH") dedicated for DNA samples, the LFH may be inactivated by UV illumination overnight.

To pre-treat the harvest samples, thaw harvest samples at room temperature for maximum of one hour. Pipette the samples (100 µl/well) on a 96 well plate: NC to well A4. RS_1, RS_2, PC_1, PC_2, TS1_1 and TS1_2 to column 1 on wells B1-G1. Rest of the TSs to column 6 on wells A6-H6. Add Proteinase K (1 µl/well) to used wells. Seal the plate tightly with optical adhesive cover. Vortex gently and spin shortly. Run the plate with Applied Biosystems 7500 Real-Time PCR system with the latest version of SDS template document "Prot K". The run program is as follows: Incubate for 60 min at +50° C. Incubate for 20 min at +95° C. Cool the samples down to +4° C. If not continuing straight to sample dilutions, store the plate in refrigerator.

For sample dilution, samples need to be diluted to fall on dynamic range of ddPCR analysis. Dilutions of 1:1000 and 1:10000 are used in the analysis. If none of these dilutions is acceptable, higher or lower dilutions can be tested. Pipette cell culture medium (90 µl/well) on wells B2-G5 of the 96 well plate with pre-treated harvest samples. Pipette cell culture medium (90 µl/well) on wells A7-H10. Pipette cell culture medium (90 µl/well) on well H4. This well will be used to prepare NTC for ddPCR analysis. Mix pre-treated samples on columns 1 and 6 thoroughly by pipetting. Prepare dilution series from column 1 all the way to column 5 and from column 6 all the way to column 10. Pipette 10 µl from column 1 to column 2 and mix the prepared dilution thoroughly by pipetting. Pipette 10 µl from column 2 to column 3 and mix. Continue until column 5 is ready and mixed. Repeat the same for columns 6-10. If not continuing straight to ddPCR analysis store the plate in refrigerator.

Preparing the ddPCR Plate:

To prepare a ddPCR plate, a fresh 1 pg/µl dilution of ARM DNA is prepared from 10 ng/µl aliquot for each RCA assay aiming to product release. See Table V for dilution series of ARM DNA.

TABLE V

Dilution series to prepare ARM DNA to be used as PC in ddPCR analysis

| Name | Dilution factor | Dilution to be used | Volume of dilution (µl) | Volume of water (µl) | Total volume (µl) | Final concentration |
|---|---|---|---|---|---|---|
| Dil1 | 10 | Neat | 2 | 18 | 20 | 1 ng/µl |
| Dil2 | 10 | Dil1 | 5 | 45 | 50 | 0.1 ng/µl |
| Dil3 | 10 | Dil2 | 10 | 90 | 100 | 10 pg/µl |
| ARM DNA | 10 | Dil3 | 10 | 90 | 100 | 1 pg/µl |

Each dilution needs to be thoroughly mixed by pipetting before using it to prepare the next one. The dilutions are prepared in DNA LFH. The last dilution named ARM DNA (1 pg/µl) is used in ddPCR run. Volume to be used is 5 µl i.e., 5 pg of ARM DNA is used in each reaction.

Fresh dilutions of Forward primer, Reverse primer and TaqMan probe for RCA are prepared for each RCA assay aiming to product release. In our experiments, we used an E1-deleted adenovirus, and thus as used as Forward primer for RCA, 5'-AAC CAG TTG CCG TGA GAG TTG-3'; as Reverse primer for RCA, 5'-CTC GTT AAG CAA GTC CTC GAT ACA-3' and as TaqMan probe for RCA, 5'-TGG GCG TCG CCA GGC TGT G-3'. The reagents are thawed at room temperature, mixed and spun down (e.g. with centrifuge/vortexer). See Table VI for dilution instructions.

TABLE VI

Dilutions of Forward primer for RCA, Reverse primer for RCA and TaqMan probe for RCA

| Reagent | Dilution factor | Original concentration | Volume of reagent (µl) | Volume of water (µl) | Total volume (µl) | Final concentration |
|---------|----------------|----------------------|----------------|----------------|----------------|-------------------|
| Forward | 16.7 | 100000 nM | 19 | 297 | 316 | 6000 nM |
| Reverse | 16.7 | 100000 nM | 19 | 297 | 316 | 6000 nM |
| Probe   | 40   | 100000 nM | 8  | 312 | 320 | 2500 nM |

The dilutions are prepared in Master mix laminar. Final concentrations of the primers (6000 nM) and the probe (2500 nM) are used in ddPCR run. Volume of 2.5 µl of each reagent is added to reaction mixture with total volume of 25 The concentrations in reaction mixture are 600 nM for the primers and 250 nM for the probe. For analytical development, in-process samples and characterization purposes, earlier prepared dilutions stored at −20° C. can be used. Master mix is prepared in LFH dedicated for master mix preparation. The sample are added on the plate in DNA LFH. Separate materials, pipettes and centrifuge/vortexers are used for master mix and DNA work. Calculate the needed well amount and the needed total volume of master mix. Thaw the ddPCR supermix for probes at room temperature and vortex at high speed when thawed. Mix the diluted Forward primer, Reverse primer and TaqMan probe for RCA and spin the reagents down. We found that a centrifuge/vortexer can be conveniently used for mixing and spinning. Prepare the master mix for ddPCR as per Table VII, and vortex at high speed.

TABLE VII

Components of master mix for ddPCR.

| Reagent | Volume/reaction (µl) | Volume required for 113 reactions (µl) |
|---------|--------------------|----------------------------------------|
| ddPCR supermix for probes | 12.5 | 1412.5 |
| Forward primer for RCA | 2.5 | 282.5 |
| Reverse primer for RCA | 2.5 | 282.5 |
| TaqMan probe for RCA | 2.5 | 282.5 |
| Total volume | 20 | 2260 |

The example is for maximum number of test samples. Modify the volumes as needed.

Pipette the master mix (20 µl/well) on wells of a 96 well plate. Optionally, the master mix can be poured on a reagent reservoir and a multichannel pipette can be used to pipette the mixture on the plates. Add ddPCR Buffer Control Kit (BC, 25 µl/well) on wells H4-H6 and on wells not needed for samples. For maximum number of test samples, note that all wells of each column need to be filled. ddPCR Buffer Control Kit ("BC") is used on wells not needed for samples. We prefer to use wells with e.g., 1:1000 and 1:10000 dilutions.

We prefer to mix the 96 well plate with pre-treated samples and dilutions by vortexing and spin the samples down. Add samples (5 µl/well) to the ddPCR plate with the master mix (20 µl/well). After usage, store the sample plate in refrigerator. The samples can be used to repeat the ddPCR analysis.

For control, mix ARM DNA dilution by pipetting and add (5 µl/well) to the ddPCR plate (wells A4, A5 and A6).

Seal the plate with Heatfoil using a plate sealer at +180° C. for 5 seconds. Vortex the plate briefly and spin the sample mixtures down. Continue to droplet generation and PCR run.

Droplet Generation, PCR Reading and Droplet Reading:

We prefer to perform automated droplet generation with an AutoDG™ device. To do so, we seal the plate with droplets with Heatfoil, using a plate sealer at +180° C. for 5 seconds. Then continue with PCR run. We prefer to run the plate with C1000™ Touch Thermal Cycler with and PCR conditions as provided in Table VIII.

TABLE VIII

PCR conditions for RCA assay

| Step | Used conditions | | | |
|------|-----------|------|------|--------|
|      | Temperature | Time | Ramp | Cycles |
| Initial denaturation | +95° C. | 10 min | 2° C./s | 1 |
| Denaturation | +94° C. | 30 s | 2° C./s | 40 |
| Annealing/extension | +60° C. | 1 min | 2° C./s | |
| Enzyme deactivation | +98° C. | 10 min | 2° C./s | 1 |
| Hold | +4° C. | ∞ | N/A | 1 |

Temperature of the lid is set to +105° C.
Sample volume is 40 µl because the AutoDG device combines 20 µl of reaction mixture with 20 µl of AutoDG oil.

Figure 2:
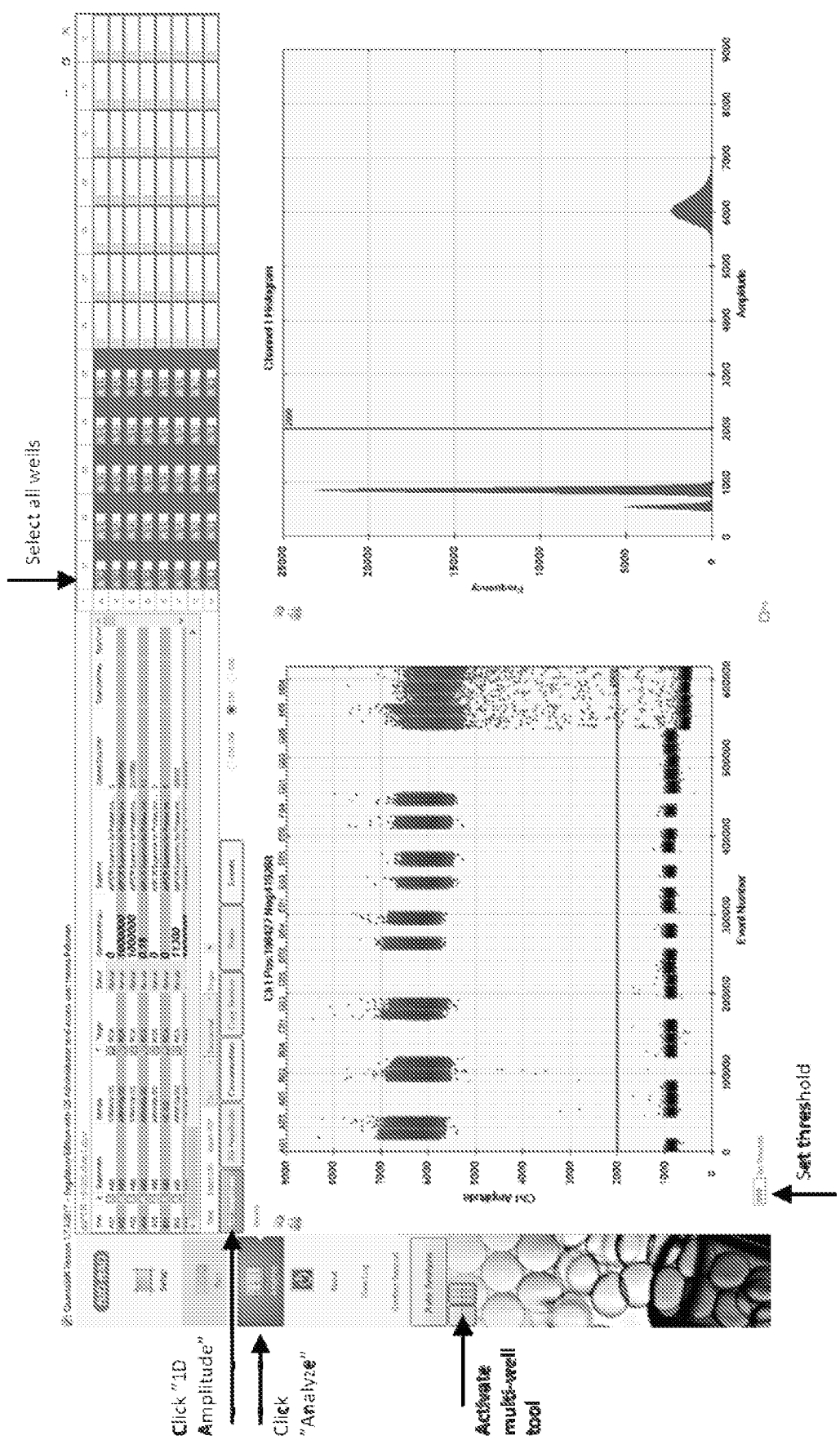
FIG. 2 is a color photograph or reprint of the QuantaSoft software user interface.

After the PCR run the droplets are stable. The plate can be stored in refrigerator overnight. Read the droplets with Droplet Reader with the latest version of QuantaSoft template "RCA ddPCR". QuantaSoft software automatically creates a folder for the run and saves the run as QuantaSoft plate document. After the run, set threshold manually at 2000 for all the wells as follows: Click "Analyze" button on the left-hand menu; Select all the wells from plate layout on the right-hand upper corner; Select "1D amplitude" display; On the bottom of the left-hand menu, activate a button with yellow markings (multi-well tool). This allows you to set the threshold for all the wells simultaneously. Set the threshold by entering 2000 to Set Threshold box (press Enter). See FIG. 2 for visualization of threshold setting and a more detailed description of the software user interface. Close the QuantaSoft software and click "Yes" as the software prompts to select "Save plate information?". Copy the created folder to server and ensure that it has the assay run number as folder name.

ddPCR run data is automatically analyzed by QuantaSoft software. Fulfillment of SSC is evaluated and the results are read with the software.

Data Analysis:

In ddPCR technique sample DNA is randomly divided between thousands of droplets. Accuracy of the analysis is the better the more droplets are present. The QX200 ddPCR system is capable to generate and read over 20 000 droplets per well. To secure the desired accuracy a criterion of ≥8000 accepted droplets is set for each analysed well. However the assay does not fail although individual wells fails this criterion. The failing wells are omitted from the further analysis. Each sample is analyzed on triplicate wells in ddPCR analysis. The result of the sample can be read if at least two of the triplicate wells have 8000 accepted droplets. To check the number of accepted droplets proceed as follows: Open the plate document (with threshold 2000) saved on the server. Click "Analyze" button on the left-hand menu. Select all the wells from plate layout on the right-hand upper corner. Select "Events" display. Tick "total" box on the right. For clarity other boxes (pos/neg) should not be ticked. Check from the values on the histogram that each well has ≥8000 accepted droplets.

System suitability criteria for NC, NTC and ARM DNA are that at least two of the triplicate wells have ≥8000 accepted droplets. Check if the criteria passes. If the criteria fails, the ddPCR analysis needs to be repeated. When considering further SSC, take only the wells with ≥8000 accepted droplets into account.

In ddPCR analysis, a sample having 5 positive droplets is considered negative. Samples having 6-34 positive droplets cannot be considered negative but might be contaminated or represent very low amount of the target DNA. Samples having 35 positive droplets are considered clearly positive. the number of positive and negative droplets on each well is checked by the procedure described above a)-e) but ticking pos or neg boxes instead of total.

Assay SSC for NC, NTC and ARM DNA are: Any of the accepted wells of NC sample has no more than 5 positive droplets, or Any of the accepted wells of NTC has no more than 5 positive droplets, or At least two of the triplicate wells of ARM DNA show 35 positive droplets.

If these SSC fail, we prefer that the ddPCR be repeated. If NC still fails, we suggest that the whole RCA assay starting from the first infection be repeated. If the reason for the failure is NTC or ARM DNA, the RCA amplification might have been successful but there is something wrong with the ddPCR analysis. In the case of repeated failure of NTC or ARM DNA, the reason for the failure needs to be investigated.

In order to read the result of a certain sample, the sample should have both positive and negative droplets. The accuracy of the analysis is compromised if the amount of negative droplets is low. The well should show >100 negative droplets. Otherwise the well is considered as "saturated" and the result of that well cannot be read.

Dynamic range of ddPCR analysis is narrow. RS and TSs are analyzed as two dilutions: 1:1000 and 1:10000. At least one of the dilutions needs to be within the range. Criteria for acceptable RS dilution are that at least two of the triplicate wells show ? 8000 accepted droplets, >100 negative droplets (the well is not saturated) and ? 35 positive droplets (the well shows positive result).

Evaluate assay SSC with the acceptable dilution(s). Assay SSC for RS is: Both RS_1 and RS_2 show positive result (≥35 positive droplets) at acceptable dilution(s) on acceptable wells. SSC passes if both RS_1 and RS_2 have at least one acceptable dilution. The reason for SSC failure can be inappropriate dilution. The used dilutions may be too low (the wells saturate) or too high (negative results). In this case, the ddPCR can be repeated with adjusted dilutions. Dilutions 1:10 and/or 1:100 from the pre-treatment plate can be used as appropriate or a further dilution from 1:10000 can be prepared. Consult a specialist to decide how to proceed. If one of replicative flasks (RS_1 or RS_2) still shows negative result while the other is within the dynamic range, the whole RCA assay starting from first infection needs to be repeated.

Criteria for acceptable TS dilution is that at least two of the triplicate wells show ≥8000 accepted droplets and >100 negative droplets (the well is not saturated). Evaluate sample SSC with the acceptable dilution(s). Note that TS are not required to pass the criteria of ≥35 positive droplets as TS may be free of RCA.

Sample SSC is: Both TSX_1 and TSX_2 have at least one acceptable dilution. If the sample fails SSC, its result cannot be reported and the sample needs to be re-analysed. However the results of the other samples can be read and reported. The reason for SSC failure can be inappropriate dilution. The used dilutions may be too low (the wells saturate). In this case, the ddPCR can be repeated with adjusted dilutions. Further dilution from 1:10000 can be prepared.

Results of RCA Assay:

The result of ddPCR analysis is given as copies/µl. QuantaSoft software reports this value for each well on Results table on the left-hand upper corner. The value is 0 if there is no positive droplets on the well and the value is 1000000 (saturated) if there is no negative droplets on the well. To calculate the results of RS and TS, record the concentration (copies/µl) reported in Results table of QuantaSoft software for each well. Record only the concentrations for the accepted wells and dilutions; otherwise mark N/A. Then calculate the adjusted concentration (copies/µl) by multiplying the reported concentration by dilution factor. Then calculate the average (copies/µl) of the adjusted concentrations. Record it with as whole number without decimals. Note that if one of the replicative flask of a certain TS (TSX_1 or TSX_2) gives a negative result with both dilutions, the average is calculated from the positive flask. For RS, calculate the RS range as average±20%: the lower end of the range is 0.8×Average, and the higher end of the range is 1.2×Average. Results of TS are compared to this RS range. For each TS, compare average to RS range. If the average is below RS range, the results is "LESS RCA than in RS". If the average is within RS range, the result is "EQUAL AMOUNT of RCA as in RS". If the average is above RS range, the result is "MORE RCA than in RS".

If one of the replicative flask of a certain TS (TSX_1 or TSX_2) gives a negative result with both dilutions and the other gives clearly positive result, the average (copies/µl) is based on the positive flask. If the comparison to RS range gives a result of "MORE RCA than in RS", the ddPCR analysis needs to be repeated. If the result is still the same, the whole RCA assay starting from the first infection needs to be repeated.

Assay results may be trended to an Excel™ file. We prefer that the following parameters are trended:
RCA assay running number
Assay SSC PASS/FAIL
Reason for possible SSC failure
Result (copies/µl) of ARM DNA
Acceptable dilutions for RS and PC
Average (copies/µl) for RS and PC (Note that average for PC is calculated in trending excel only.)

Based on our disclosure, the artisan may easily make variations to it. for example, while we have in fact developed our improved assay using recombinant adenovirus bearing a transgene for vascular endothelial growth factor D, our assay can also identify replication-competent contaminant virus in vector with other transgenes (e.g., p53, interferon etc).

"Infection" refers to a virus replicating in a target cell to form progeny. In contrast, "transfection" refers to delivery via a viral vector of foreign DNA or RNA into a target cell. Transfection does not require the virus replicate in the target cell.

Similarly, while we in fact tested our assay on a viral vector intended to not replicate at all in a human patient, our assay can as readily be used on viral vector intended to replicate conditionally, e.g., to replicate only in cancerous human cells but not in normal human cells. We thus use the phrase "unable to replicate in normal human cells" in the appended legal claims to indicate this.

Similarly, while our experiments have been done on adenovirus, our method is as readily useful for other types of gene therapy viral vectors.

We thus intend the legal coverage of our patent to be defined not by our specific laboratory work described above, but by our appended legal claims and their permissible equivalents.

We claim:

1. A method for identifying presence of replication-competent virus in a sample of replication-deficient virus, the method comprising:
   a. incubating live target cells with the sample to produce transduced cells;
   b. lysing the transduced cells to produce a transduced cell lysate;
   c. infecting assay cells with the transduced cell lysate;
   d. lysing the assay cells to produce an assay cell lysate;
   e. removing cellular debris from the assay cell lysate to produce an assay supernatant; and
   f. adding a mixture comprising a probe directly to the assay supernatant, wherein the probe binds to a region of the viral genome of the replication-competent virus essential for viral replication and is detected using a method that comprises digital PCR, wherein,
      if replication-competent virus is present in the sample, detecting binding of the probe to the region of the viral genome indicates presence of replication-competent virus in the sample; and
      if replication-competent virus is not present in the sample, not detecting binding of the probe to the region of the viral genome indicates absence of replication-competent virus in the sample.

2. The method of claim 1, wherein the replication-deficient virus is adenovirus and wherein the mixture comprises SEQ ID NO. 1, SEQ ID NO. 2 and SEQ ID NO. 3.

3. The method of claim 1, wherein the method detects 25 or fewer of a replication-competent viral particle per $3 \times 10^{10}$ of a replication-deficient viral particle.

4. The method of claim 1, wherein the replication-competent virus and replication-deficient virus comprise a transgene that encodes a polypeptide selected from the group consisting of: interferon and p53.

5. The method of claim 3, wherein the method detects 7 or fewer of the replication-competent viral particle per $3 \times 10^{10}$ of the replication-deficient viral particle.

6. The method of claim 1, wherein the replication-deficient virus comprises a mutation or deletion within the region of the viral genome of the replication-competent virus essential for viral replication.

7. The method of claim 6, wherein the replication-competent virus comprises a reversion of the mutation or deletion to the wild-type viral genome.

8. The method of claim 1, further comprising determining the approximate quantity of the replication-competent viral particle in the sample.

9. The method of claim 1, wherein binding of the probe to the region of the viral genome is detected using a method that comprises droplet digital PCR (ddPCR).

10. The method of claim 1, further comprising pretreating the assay supernatant with a proteinase K to release a viral DNA encapsulated inside the replication-competent viral particle.

* * * * *